(12) United States Patent
Shah et al.

(10) Patent No.: US 6,881,536 B1
(45) Date of Patent: Apr. 19, 2005

(54) PARTICLE BASED ELECTROCHEMILUMINESCENT ASSAYS

(75) Inventors: Haresh P. Shah, Gaithersburg, MD (US); Lee O. Hall, Miami Lakes, FL (US); Michael J. Powell, Danville, CA (US); Richard J. Massey, Rockville, MD (US)

(73) Assignee: BioVeris Corporation, Gaithersburg, MD (US)

( * ) Notice: Subject to any disclaimer, the term of this patent is extended or adjusted under 35 U.S.C. 154(b) by 0 days.

(21) Appl. No.: 08/413,536

(22) Filed: Mar. 30, 1995

Related U.S. Application Data

(63) Continuation of application No. 08/090,467, filed on Jul. 12, 1993, now abandoned, which is a continuation of application No. 07/539,389, filed on Jun. 18, 1990, now abandoned, which is a continuation of application No. 07/266,822, filed on Nov. 3, 1988, now Pat. No. 4,928,529, and a continuation-in-part of application No. 07/117,017, filed on Nov. 4, 1987, now abandoned, and a continuation-in-part of application No. PCT/US87/09870, filed on Apr. 30, 1987, and a continuation-in-part of application No. 07/369,560, filed on Dec. 18, 1987, now abandoned, which is a continuation-in-part of application No. 06/858,354, filed on Apr. 30, 1986, now abandoned.

(51) Int. Cl.[7] .................... G01N 33/543; G01N 33/546; G01N 33/548; G01N 33/551; G01N 33/569
(52) U.S. Cl. ................. 435/5; 435/6; 435/7.1; 435/7.2; 435/7.5; 436/501; 436/518; 436/524; 436/528; 436/529; 436/530; 436/534; 436/536; 436/805; 436/806
(58) Field of Search ................ 436/501–536, 436/172, 805–806; 435/5–7.95

(56) References Cited

U.S. PATENT DOCUMENTS

| | | | | |
|---|---|---|---|---|
| 3,992,517 A | * | 11/1976 | Lowke et al. ............... 430/534 |
| 4,120,945 A | * | 10/1978 | Gutcho et al. .............. 436/531 |
| 4,201,763 A | * | 5/1980 | Monthony et al. .......... 436/533 |
| 4,376,110 A | * | 3/1983 | David et al. ................ 436/513 |
| 4,547,466 A | * | 10/1985 | Turanchik et al. .......... 436/509 |
| 4,652,533 A | * | 3/1987 | Jolley ........................ 436/578 |
| 4,745,076 A | * | 5/1988 | Muller et al. ............... 436/537 |
| 5,238,808 A | * | 8/1993 | Bard et al. ..................... 435/4 |
| 5,591,581 A | * | 1/1997 | Massey et al. ................. 435/6 |

FOREIGN PATENT DOCUMENTS

WO 8706706 * 11/1987

OTHER PUBLICATIONS

Webster's Ninth New Collegiate Dictionary, Merriam–Webster Inc., 1985, pp. 282 and 1312.*
Teska, JPTOS, 83, 223–228, 2001.*
E. E. Conn et al, *Outlines of Biochemistry*, Fourth Edition, John Wiley & Sons, Inc. 1976. pp. 249–251.*
B. D. Davis et al, *Microbiology*, Third Edition, Harper & Row, Publishers, Inc. 1980.*

* cited by examiner

*Primary Examiner*—David Saunders
(74) *Attorney, Agent, or Firm*—Finnegan, Henderson, Farabow, Garrett & Dunner, L.L.P.

(57) ABSTRACT

A method for the detection of an analyte of interest in a sample, which method comprises the steps of:
(1) forming a composition comprising
  (a) a sample,
  (b) at least one substance selected from the group consisting of
    (i) added analyte of interest or an analog of the analyte of interest,
    (ii) a binding partner of the analyte of interest or its said analog, and
    (iii) a reactive component capable of binding with (i) or (ii),
    wherein one of said substances is linked to a label compound having a chemical moiety capable of being induced to luminesce, and
  (c) a plurality of particles capable of specifically binding with the analyte and/or a substance defined in (b) (i), (b) (ii), or (b) (iii);
(2) inducing the label compound to luminesce; and
(3) measuring luminescence emitted by the composition to determine the presence of the analyte of interest in the sample.

94 Claims, 1 Drawing Sheet

PARTICLE BASED ELECTROCHEMILUMINESCENT ASSAYS

This application is a continuation of application Ser. No. 08/090,467, filed Jul. 12, 1993, now abandoned, which was a continuation of application Ser. No. 07/539,389 filed Jun. 18, 1990 (now abandoned), which was a continuation of application Ser. No. 07/266,822 filed Nov. 3, 1988, now U.S. Pat. No. 4,928,529 application Ser. No. 07/266,822 was a continuation-in-part of application Ser. No. 06/858,354 filed Apr. 30, 1986 (now abandoned), a continuation-in-part of application Ser. No. 07/117,017 filed Nov. 4, 1987 (now abandoned), a continuation-in-part of PCT/US87/09870 filed Apr. 30, 1987, and a continuation-in-part of application Ser. No. 07/369,560 filed Dec. 18, 1987, now abandoned.

FIELD OF THE INVENTION

This application relates generally to binding assays, more particularly to those which measure the presence of an analyte of interest by detecting or quantitating electromagnetic radiation emitted by one or more components of the assay system. More specifically, the invention relates to precise, reproducible, accurate nonseparation, specific binding assays in which electromagnetic radiation emitted by assay compositions containing electrochemiluminescent moieties.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

Electrochemiluminescent (ECL) assay techniques are an improvement on chemiluminescent techniques. They provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, reference is made to U.S. application Serial No. 06/789,113, filed October 24, 1985 now U.S. Patent No. 5,238,808, pending application Serial No. 07/993,530 filed Dec. 17, 1992, which is a continuation of Serial No. 07/675,019 filed Mar. 25, 1991, now abandoned, which is a continuation of application Serial No. 06/858,354 filed Apr. 30, 1986, now abandoned, PCT published application number U.S. 87/00987 filed Apr. 30, 1987, now abandoned, which is a continuation-in-part of U.S. national phase PCT application Ser. No. 07/369,560 filed Dec. 18, 1987 now abandoned in favor of pending continuation application Ser. No. 08/195,825 filed Feb. 10, 1994, and U.S. application Ser. No. 07/117,017 filed Nov. 4, 1987, now abandoned, in favor of U.S. application Serial No. 07/539, 389 filed Jun. 18, 1990, which is a continuation of application Ser. No. 07/266,882, filed November 3, 1988, now abandoned, which is a continuation-in-part of application Serial No. 06/858,354 filed Apr. 30, 1986, now abandoned. Reference is also made to PCT published application US85/02153 (WO86/02734), the content of which is incorporated by reference. The disclosure of the aforesaid applications is incorporated by reference.

It would be desirable to carry out electrochemiluminescent assays without the need for a separation step during the assay procedure and to maximize the signal modulation at different concentrations of analyte so that precise and sensitive measurements can be made. Among prior art methods for nonseparation assays are those which employ microparticulate matter suspended in the assay sample to bind one or more of the binding components of the assay. U.S. Pat. No. 4,305,925 relates to the detection and determination of clinically relevant proteins and peptides by means of nephelometric and turbidometric methods. The methods disclosed involve binding the antigen or antibody to latex particles which perform the function of light scattering or adsorption.

U.S. Pat. No. 4,480,042 relates to techniques employing particle reagents consisting of shell-core particles. The shell contains functional groups to which compounds of biological interest can be covalently bonded, and the high refractive index of the core results in high sensitivity to light scattering measurements. The technique is based upon agglutination reactions which result from the reaction of bivalent antibodies with multivalent antigens of interest to produce aggregates which can be detected and/or measured in various ways.

U.S. Pat. No. 4,419,453 likewise relates to the use of colored latex agglutination test methods useful for detecting the presence of immunochemicals such as antibodies and immunogens.

The assay techniques of the prior art and the use of microparticulate matter in the assay medium would not appear applicable for assays wherein a luminescent phenomenon is measured. One would expect that the luminescence from free chemiluminescent or electrochemiluminescent moieties would be absorbed, scattered, or otherwise suffer interference from the microparticulate matter.

OBJECTS OF THE INVENTION

It is an object of this invention to provide nonseparation, electrochemiluminescent specific binding assay methods and reagent compositions for the detection of small to large analytes present over a wide concentration range in test samples.

It is a second object of this invention to provide an assay method and reagent composition giving improved performance, including faster assay time, greater sensitivity and greater precision, compared to conventional nonseparation assay methods and reagents.

It is an additional object of this invention to provide an assay method based upon a binding reaction and the measurement of luminescence for detecting various analytes ranging in molecular sizes and concentrations.

These and other objects and advantages of the present invention will become more readily apparent after consideration of the following description of the invention.

STATEMENT OF THE INVENTION

In one aspect the present invention is directed to a sensitive, specific binding assay method based on a luminescent phenomenon wherein inert microparticulate matter is specifically bound to one of the binding reactants of the assay system. The invention may be used in a heterogeneous (one or more separation steps) assay format and may be used most advantageously in a homogeneous (nonseparation) assay format.

In a further aspect, the invention relates to a composition for an assay based upon a binding reaction for the measurement of luminescent phenomenon, which composition includes a plurality of suspended particles having a surface capable of binding to a component of the assay mixture.

In an additional aspect, the invention is directed to a system for detecting or quantitating an analyte of interest in a sample, which system is capable of conducting the assay methods of the invention using the assay compositions of the inventions. The system includes means for inducing the label compound in the assay medium to luminesce, and means for measuring the luminescence to determine the presence of the analyte of interest in the sample.

Surprisingly, it has now been found that the binding of that component of the assay system to which an electrochemiluminescent moiety has been linked, to suspended microparticulate matter, greatly modulates the intensity of the luminescent signal generated by the electrochemiluminescent moiety linked to that component, thereby providing a means of monitoring the specific binding reaction of the assay system. Even more surprisingly, the suspended particles have been found to have little or no effect on the intensity of the luminescent signal generated by the electrochemiluminescent moiety linked to the component of the system which remains unbound to the suspended microparticulate matter.

Thus, the invention is directed to a method for the detection of an analyte of interest in a sample, which method includes the steps of (1) forming a composition comprising (a) a sample suspected of containing an analyte of interest, (b) at least one substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a substance defined in (b)(i), (ii), or (iii); (2) inducing the label compound to luminesce; and (3) measuring the luminescence emitted by the composition to determine the presence of the analyte of interest in the sample.

Analogs of the analyte of interest, which may be natural or synthetic, are compounds which have binding properties comparable to the analyte, but include compounds of higher or lower binding capability as well. Binding partners suitable for use in the present invention are well-known. Examples are antibodies, enzymes, nucleic acids, cofactors and receptors. The reactive components capable of binding with the analyte and/or with a binding partner thereof may be a second antibody or a protein such as Protein A or Protein G or may be avidin or biotin or another component known in the art to enter into binding reactions.

It is within the scope of the invention that the methods, assay compositions, assay reagents and systems provided herein may be utilized to quantify an analyte of interest. Accordingly, the invention further provides a method for the detection and quantitation of an analyte of interest in a sample, which method includes the steps of: (1) combining (a) a sample suspected of containing an analyte of interest, (b) a known amount of at least one substance selected from the group consisting of (i) added analyte of interest or analog of the analyte of interest, (ii) a binding partner of the said analyte of interest or its said analog, and (iii) a reactive component capable of binding with (i) or (ii), wherein one of said substances is linked to a label compound having a chemical moiety capable of being induced to luminesce, and (c) a known amount of suspended particles capable of specifically binding with the analyte and/or a substance defined in (b)(i), (ii), or (iii); (2) inducing the label compound to luminesce; and (3) comparing the luminescence in the mixture to the luminescence in a mixture containing a known amount of the analyte of interest.

Advantageously, the luminescence arises from electrochemiluminescence (ECL) induced by exposing the label compound, whether bound or unbound to specific binding partners, to a voltammetric working electrode. The ECL reactive mixture therefore is controllably triggered to emit light by a voltage impressed on the working electrode at a particular time and in a particular manner to generate light.

Herein, the term "ECL moiety", "metal-containing ECL moiety" "label", "label compound", and "label substance", are used interchangeably. It is within the scope of the invention for the species termed "ECL moiety", "metal-containing ECL moiety", "organometallic", "metal chelate", "transition metal chelate" "rare earth metal chelate", "label compound", "label substance" and "label" to be linked to other molecules such as an analyte or an analog thereof, binding partner of the analyte or an analog thereof, and further binding partners of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog.

It is similarly within the scope of the invention for the aforementioned "composition" or "system" to contain unstable, metastable and other intermediate species formed in the course of the ECL reaction, such as an ECL moiety in an excited state as aforesaid and the above-mentioned strong reducing agent.

Additionally, although the emission of visible light is an advantageous feature of certain embodiments of the invention it is within the scope of the invention for the composition or system to emit other types of electromagnetic radiation, such as infrared or ultraviolet light, X-rays, microwaves, etc. Use of the terms "electrochemiluminescence", "electrochemiluminescent" "electrochemiluininesce" "luminescence", "luminescent", and "luminesce" in connection with the present invention does not require that the emission be light, but admits of the emission's being such other forms of electromagnetic radiation.

DESCRIPTION OF CERTAIN PREFERRED EMBODIMENTS

Figure 1:
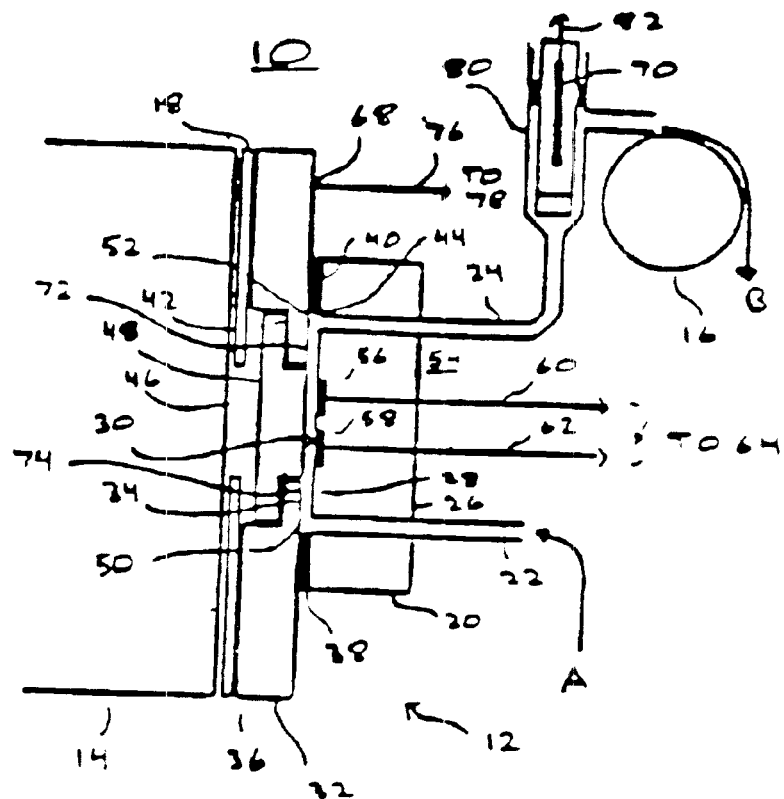
FIG. 1 is a schematic drawing of an electrochemiluminescence cell for performing the microparticulate-based nonseparation assays of the invention.

The invention, as well as other objects and features thereof, will be understood more clearly and fully from the following description of certain preferred embodiments.

The invention as it relates to nonseparation binding assay methods, assay compositions, assay reagents and systems is broadly applicable to analytes of interest which are capable of entering into binding reactions. These reactions include, e.g., antigen-antibody, ligand receptor, DNA and RNA interactions, and other known reactions. The invention relates to different methods and assays for qualitatively and quantitatively detecting the presence of such analytes of interest in a multicomponent sample.

In addition to the metal-containing ECL moieties, typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, nonbiological polymer (preferably soluble), synthetic organic molecule, organometallic molecule, tranquilizer, barbituate, alkaloid, steroid, vitamin, amino acid, sugar, lectin, recombinant or derived protein, biotin, avidin, streptavidin, or inorganic molecule present in the sample.

Typically, the analyte of interest is present at a concentration of $10^{-3}$ molar or less, for example, at least as low as $10^{-18}$ molar.

The reagent which is combined with the sample containing the analyte of interest contains at least one substance selected from the group consisting of (i) added analyte of interest or its analog, as defined above, (ii) a binding partner of the analyte of interest or its said analog, and (iii) a reactive component, as defined above, capable of binding with (i) or (ii), wherein one of said substances is linked to an ECL moiety capable of being induced to luminesce. For example, the labeled substance may be a whole cell or surface antigen, a subcellular particle, virus, prion, viroid, antibody, antigen, hapten, lipid, fatty acid, nucleic acid, polysaccharide, protein, lipoprotein, lipopolysaccharide, glycoprotein, peptide, polypeptide, cellular metabolite, hormone, pharmacological agent, tranquilizer, barbiturate, alkaloid, steroid, vitamin, amino acid, sugar, nonbiological polymer (preferably soluble), lectin, recombinant or derived protein, synthetic organic molecule, organometallic molecule, inorganic molecule, biotin, avidin or streptavidin. In one embodiment, the reagent is an electrochemiluminescent moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

An essential feature of the invention is the utilization of metal-containing ECL moieties which are capable of electrochemiluminescence (ECL). These encompass organometallic compounds which luminesce, such as 4,4',5',5 tetramethyl bipyridine Re(I)(4-ethyl pyridine)$(CO)_3{}^+CF_3SO_3$; and Pt2-(2-thienyl)$_2$ pyridine.

Advantageously, the ECL moieties are metal chelates. The metal of that chelate is suitably any metal such that the metal chelate will luminesce under the electrochemical conditions which are imposed on the reaction system in question. The metal of such metal chelates is, for instance, a transition metal (such as a d-block transition metal) or a rare earth metal. The metal is preferably ruthenium, osmium, rhenium, iridium, rhodium, platinum, indium, palladium, molybdenum, technetium, copper, chromium or tungsten. Especially preferred are ruthenium and osmium.

The ligands which are linked to the metal in such chelates are usually heterocyclic or organic in nature, and play a role in determining whether or not the metal chelate is soluble in an aqueous environment or in an organic or other nonaqueous environment. The ligands can be polydentate, and can be substituted. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis [(4,4'-carbomethoxy)-2,2'-bipyridinel]2-[3-(4-methyl-2,2'-bipyridine-4-yl)propyl]-1,3-dioxolane ruthenium (II); bis (2,2'bipyridine)

[4-(butan-1-al)-4'-methyl-2,2'-bipyridine] ruthenium (II); bis (2,2'-bipyridine).

[4-(4'-methyl-2,2'-bipyridine-4'-yl)-butyric acid] ruthenium (II); (2,2'-bipyridine)

[bis-bis(1,2-diphenylphosphino)ethylene] 2-[3-(4-methyl-2,2'-bipyridine-4'-yl)propyl]-1,3-dioxolane osmium (II); bis (2,2'-bipyridine)

[4-(4'-methyl-2,2'-bipyridine)-butylamine] ruthenium (II); bis (2,2'-bipyridine)

[1-bromo-4(4'-methyl-2,2'-bipyridine-4-yl)butane] ruthenium (II); bis (2,2'-bipyridine)maleimidohexanoic acid, 4-methyl-2,2'-bipyridine-4'-butylamide ruthenium (II).

Other ECL moieties are described in commonly assigned PCT application Ser. No. US87/00987 filed Apr. 30, 1987, now abandoned and U.S. application Ser. No. 117,017 filed Nov. 4, 1987, now abandoned in favor of application Ser. No. 08/227,898 filed Apr. 15, 1994, which is a continuation of application Ser. No. 07/533,931 filed Jun. 5, 1990.

The function of the ECL moieties in the present invention is to emit electromagnetic radiation as a result of introduction into the reaction system of electrochemical energy. In order to do this, they must be capable of being stimulated to an excited energy state and also capable of emitting electromagnetic radiation, such as a photon of light, upon descending from that excited state. While not wishing to be bound by theoretical analysis of the mechanism of the ECL moiety's participation in the electrochemiluminescent reaction, we believe that it is oxidized by the introduction of electrochemical energy into the reaction system and then, through interaction with a reductant present in the system, is converted to the excited state. This state is relatively unstable, and the metal chelate quickly descends to a more stable state. In so doing, the chelate gives off electromagnetic radiation, such as a photon of light, which is detectable.

The ECL moiety is linked, as taught in the parent applications, to at least one substance selected from the group consisting of (i) added analyte of interest or its analog, (ii) a binding partner of the analyte of interest or its said analog, and (iii) a reactive compound capable of binding with (i) or (ii).

Analogs of the analyte of interest, which can be natural or synthetic, are typically compounds which have binding properties comparable to the analyte, but can also be compounds of higher or lower binding capability. The reactive components capable of binding with the analyte or its analog, and/or with a binding partner thereof, and through which the ECL moiety can be linked to the analyte, is suitably a second antibody or a protein such as Protein A or Protein G, or avidin or biotin or another component known in the art to enter into binding reactions.

The amount of metal chelate or other metal-containing ECL moiety incorporated in accordance with the invention will vary from system to system. Generally, the amount of such moiety utilized is that amount which is effective to result in the emission of a detectable, and if desired, quantitatable, emission of electromagnetic energy, from the aforementioned composition or system. The detection and/or quantitation of an analyte of interest is typically made from a comparison of the luminescence from a sample containing an analyte of interest and an ECL moiety to the luminescence emitted by a calibration standard developed with known amounts of the analyte of interest and ECL moiety. This assumes a homogeneous format. In the heterogeneous mode, a separation as discussed previously is carried out prior to ECL analysis.

As can be appreciated by one of ordinary skill in the art, the identity and amount of the metal-containing ECL moiety will vary from one system to another, depending upon prevailing conditions. The appropriate metal-containing ECL moiety, and sufficient amount thereof to obtain the desired result, can be determined empirically by those of ordinary skill in the art, once equipped with the teachings herein, without undue experimentation.

The sample which may contain the analyte of interest, which may be in solid, emulsion, suspension, liquid, or gas form, may be derived from, for example, cells and cell-derived products, water, food, blood, serum, hair, sweat, urine, feces, tissue, saliva, oils, organic solvents or air. The sample may further comprise, for example, water, acetonitrile, dimethyl sulfoxide, dimethyl formamide, n-methyl-pyrrolidone or alcohols.

The particles advantageously comprise microparticulate matter having a diameter of 0.05 $\mu$m to 200 $\mu$m, preferably 0.1 $\mu$m to 100 $\mu$m, most preferably 0.5 $\mu$m to 10 $\mu$m, and a surface component capable of binding to the analyte and/or one or more of the other substances defined in subparagraphs (b)(i), (b)(ii), or (b)(iii) above. For example, the microparticulate matter may be crosslinked starch, dextrans, cellulose, proteins, organic polymers, styrene copolymer such as styrene/butadiene copolymer, acrylonitrile/butadiene/styrene copolymer, vinylacetyl acrylate copolymer, or vinyl chloride/acrylate copolymer, inert inorganic particles, chromium dioxide, iron oxide, silica, silica mixtures, and proteinaceous matter, or mixtures thereof. Desirably, the particles are suspended in the ECL system.

The method of the invention may be used in heterogeneous assay formats where the ECL moiety (e.g. label compound) is first separated from the assay mixture before electrochemiluminescence is induced and measured, or, advantageously, it may be used in homogeneous assay formats, where luminescence is induced and measured in the assay mixture.

In order to operate a system in which an electrode introduces electrochemical energy, it is necessary to provide an electrolyte in which the electrode is immersed and which contains the ECL moiety. The electrolyte is a phase through which charge is carried by ions. Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid—e.g., a liquid, a vapor, or a supercritical fluid—or may be a solution of one or more substances in a solid, a vapor or supercritical fluid.

The electrolyte is suitably a solution of a salt in water. The salt can be a sodium salt or a potassium salt preferably, but incorporation of other cations is also suitable in certain embodiments, as long as the cation does not interfere with the electrochemiluminescent interaction sequence. The salt's anion may be a phosphate, for example, but the use of other anions is also permissible in certain embodiments of the invention—once again, as long as the selected anion does not interfere with the electrochemiluminescent interaction sequence.

The composition may also be nonaqueous. While supercritical fluids can in certain instances be employed advantageously, it is more typical to utilize an electrolyte comprising an organic liquid in a nonaqueous composition. Like an aqueous electrolyte, the nonaqueous electrolyte is also a phase through which charge is carried by ions. Normally, this means that a salt is dissolved in the organic liquid medium. Examples of suitable organic liquids are acetonitrile, dimthylsulfoxide (DMSO), dimethylformamide (DMF), methanol, ethanol, and mixtures of two or more of the foregoing. Illustratively, tetraalkylammonium salts, such as tetrabutylammonium tetrafluoroborate, which are soluble in organic liquids can be used with them to form nonaqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

As described in commonly assigned U.S. application Ser. No. 08/196,315, now abandoned, which is a continuation of U.S. application Ser. No. 07/266,914 filed Nov. 3, 1988, now abandoned, which is a continuation-in-part of Ser. No. 07/117,017 filed Nov. 4, 1987, which is in turn is a continuation-in-part of Ser. No. 06/858,354, filed Apr. 30, 1986, now abandoned, entitled Electrochemiluminescent Reaction Utilizing Amine-Derived Reductant, naming Leland and Powell as inventors, it is desirable to include a reductant, typically an amine or amine moiety (of a larger molecule) which can be oxidized to convert it to a highly reducing species. The subject matter of this application is incorporated by reference. It is believed that the amine or amine moiety is also oxidized by electrochemical energy introduced into the reaction system. The amine or amine moiety loses one electron, and then deprotonates, or rearranges itself, into a strong reducing agent. This agent interacts with the oxidized metal-containing ECL moiety and causes it to assume the excited state discussed above. In order to carry out its role, the amine or amine moiety preferably has a carbon-centered radical with an electron which can be donated from such carbon, and an alpha carbon which can then act as a proton donor during deprotonation in order to form the reductant. The amine-derived reductant provides the necessary stimulus for converting the metal-containing ECL moiety to its excited state, from which detectable electromagnetic radiation is emitted.

Generally speaking, the reductant formed from the amine or amine moiety has a redox potential, $E_a$, which is defined in accordance with the following formula: $E_a \leq -hc/\lambda + K + E_m$. In the formula, h is Planck's constant, c is the speed of light, $\lambda$ is the wavelength characteristic of light emitted from the excited state of the metal-containing ECL moiety, K is the product of and the absolute temperature in degrees Kelvin of the environment in which the ECL interaction takes place and the change in entropy as a result due to the eletrochemiluminescent reaction and $E_m$ is the redox potential of the ECL moiety. Normally, the product of temperature and change in entropy is approximately 0.1 eV.

The following calculation explicates the use of the formula $$E_a \leq -\frac{hc}{\lambda} + K + E_m \tag{1}$$

for determining the minimum reducing power of the oxidized, deprotonated amine product, and thus the selection of the suitable amine or amine moieties.

For Ru(bpy)$_3^{2+}$ as ECL moiety, the wavelength of emission, $\lambda$, is 620 nM. See Tokel N. E., et al., J. Am. Chem. Soc. 94, 2862 (1972). $E_m$ is 1.3 V as compared to NHE (NHE is a normal hydrogen reference electrode)

$$\frac{hc}{\lambda} = \frac{(4.13 \times 10^{-15} \text{ eV} - \text{sec})(3 \times 10^{10} \text{ cm/sec})}{6.2 \times 10^{-5} \text{ cm}} \tag{2}$$

$$= 2.0 \text{ eV (electron volts)}.$$

See Wilkins, D. H., et al., Anal. Chim. Acta. 9, 538 (1953). K is taken to be 0.1 eV. See Faulkner, L. R., et al., J. Am. Chem. Soc. 94, 691 (1972). Substituting these values into equation 1 gives $$E_a \leq -2.0 + 0.1 + 1.3 \tag{3}$$

$$E_a \leq -0.6 \tag{4}$$

Equation 4 implies that the reducing strength of the reductant must be equal to or more negative than –0.6 V as compared to NHE. (Note that when referring to potential differences, i.e., $E_a$ or $E_m$, the unit of potential is Volts, and the terms hc/$\lambda$ and K have an energy unit which is eV; however, the conversion of potential difference to eV is unity.)

A wide range of amines and corresponding amine moieties can be utilized in practicing the present invention. Generally, the amine or amine moiety is chosen to suit the pH of the system which is to be electrochemiluminescently analyzed. Another relevant factor is that the amine or amine moiety should be compatible with the environment in which it must function during analysis, i.e., compatible with an aqueous or nonaqueous environment, as the case may be. Yet another consideration is that the amine or amine moiety selected should form an amine-derived reductant under prevailing conditions which is strong enough to reduce the oxidized metal-containing ECL moiety in the system.

Amines (and corresponding moieties derived therefrom) which are advantageously utilized in the present invention are aliphatic amines, such as primary, secondary and tertiary alkyl amines, the alkyl groups of each having from one to three carbon atoms, as well as substituted aliphatic amines. Tripropyl amine is an especially preferred amine as it leads to, comparatively speaking, a particularly high-intensity emission of electromagnetic radiation, which enhances the sensitivity and accuracy of detection and quantitation with embodiments in which it is used. Also suitable are diamines, such as hydrazine, and polyamines, such as poly (ethyleneimine). The amine substance in the present invention can also be an aromatic amine, such as aniline. Additionally, heterocyclic amines such as pyridine, pyrrole, 3-pyrroline, pyrrolidine and 1,4-dihydropyridine are suitable for certain embodiments.

The foregoing amines can be substituted, for example, by one or more of the following substituents: —OH, alkyl, chloro, fluoro, bromo and iodo, —SO$_3$, aryl, —SH,

—COOH, ester groups, ether groups, alkenyl, alkynyl,

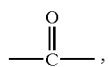

-N$_2^+$, cyano, epoxide groups and heterocyclic groups. Also, protonated salts, for instance, of the formula R$_3$N—H$^+$, wherein R is H or a substituent listed above are suitable. Amine moieties corresponding to the above-mentioned amines (substituted or unsubtituted) are also preferred.

As previously mentioned, tripropyl amine (or an amine moiety derived therefrom) is especially preferred because it yields a very high light intensity. This amine, and the other amines and the amine moieties useful in the present invention, work suitably well at pH of from 6 to 9. However, tripropyl amine gives best results at a pH of from 7–7.5. Examples of additional amines suitable for practicing the invention are triethanol amine, triethyl amine, 1,4-diazabicyclo-(2.2.2)-octane, 1-piperidine ethanol, 1,4-piperazine-bis-(ethane-sulfonic acid), tri-ispropyl amine and poly(ethyleneimine).

Typically, the metal-containing ECL moiety utilized in the present invention is the reaction-limiting constituent. Accordingly, it is also typical that the amine or amine moiety is provided in a stoichiometric excess with respect thereto. Illustratively, the amine or amine moiety is employed in a concentration of 50–150 mM. For utilization at a pH of approximately 7, a concentration of 100 mM is often advantageous. In certain embodiments, the upper limit on amine or amine moiety concentration is determined by the maximum solubility of the amine or moiety in the environment in which it is being used, for example in water. In general, the amount of amine or amine moiety employed is that which is sufficient to effect the transformation of the oxidized metal-containing ECL moiety into its excited state so that luminescence occurs. Those of ordinary skill in the art, equipped with the teachings herein, can determine empirically the amount of amine or amine moiety advantageously used for the particular system being analyzed, without undue experimentation.

As described in commonly assigned U.S. application Ser. No. 06/858,354, filed Apr. 30, 1986, now abandoned in favor of continuation-in-part application Ser. No. 07/117,017 filed Nov. 4, 1987, now abandoned in favor of pending continuation-in-part application Ser. No. 07/267,509 filed Nov. 3, 1988, now U.S. Pat. No. 5,061,445 issued Oct. 29, 1991, entitled Enhanced Electrochemiluminescent Reaction, naming Shah, von Borstel, and Tyagi as inventors, the assays of the invention are desirably carried out in the presence of an enhancer, typically a compound of the formula

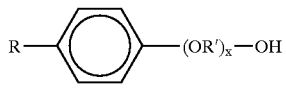

wherein R is hydrogen or $C_nH_{n2+1}$, R' is $C_nH_{2n}$, x is 0 to 70, and n is from 1 to 20. Specifically, n is from 1 to 4. Specific examples are a substance available in commerce under the name Triton X-100, of the formula

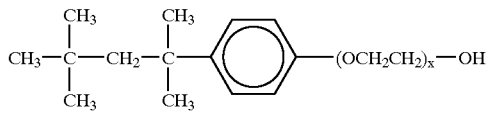

wherein x is 9–10, and a substance available in commerce under the name Triton N-401 (NPE-401), of the formula

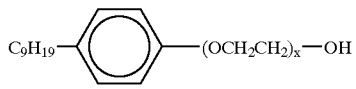

wherein x is 40. The enhancer is generally utilized in an amount sufficient so that in its presence the desired increase in emission of electromagnetic radiation occurs. Typically, the amount is 0.01% to 5.0%, more specifically 0.1% to 1.0%, v/v. The subject matter of this application is incorporated by reference.

The ECL moiety incorporated in accordance with the present invention is induced to emit electromagnetic radiation by stimulating it into an excited state. This is accomplished by exposing the system in which the ECL moiety is incorporated to electrochemical energy. The potential at which oxidation of the ECL moiety and the species forming a strong reductant occurs depends upon the exact chemical structures thereof, as well as factors such as the pH of the system and the nature of the electrode used to introduce electrochemical energy. It is well known to those of ordinary skill in the art how to determine the optimal potential and emission wavelength of an electrochemiluminescent system. Certain preferred methods of stimulating the ECL system are disclosed in commonly assigned U.S. application Ser. No. 188,258 filed Apr. 29, 1988, which is incorporated herein by reference.

Figure 2:
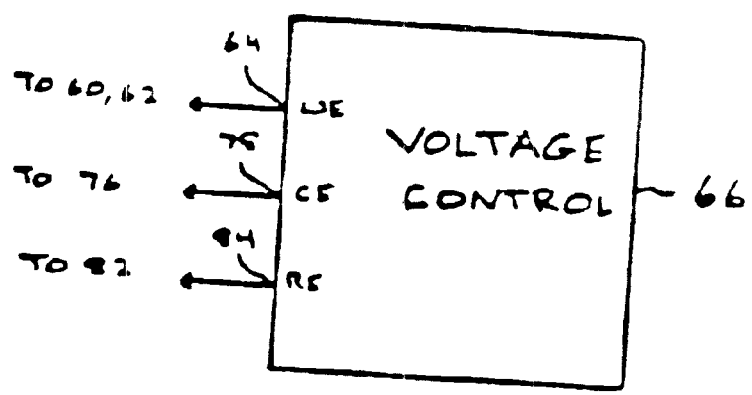
FIG. 2 is a simplified diagram of a voltage control apparatus for use with the cell of FIG. 1.

An apparatus for carrying out the assays of the invention is described in FIGS. 1 and 2. FIG. 1 discloses an advantageous ECL apparatus, but the methods of the present invention are not limited to application in apparatus 10, but rather may be employed in other types of ECL apparatus which include a working electrode or other triggering surface to provide electrochemical energy to trigger the ECL moiety into electrochemiluminescence. While the methods of the invention can be carried out in a static or flow-through mode, apparatus 10 includes a flow-through cell, which provides distinct advantages for many types of samples including binding assay samples.

Apparatus 10 includes an electrochemical cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during ECL measurement periods. The shutter mechanism may be closed, for example, during maintenance. Also included in apparatus 10 but not illustrated in FIG. 1 is a lightproof housing intended to mount the various components therein and to shield PMT 14 from any external light during the ECL measurements.

Cell 12 itself includes a first mounting block 20 through which passes an inlet tube 22 and an outlet tube 24, which may be advantageously constructed of stainless steel. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32, advantageously constructed of stainless steel also has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 30 defines part of the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34. Mounting block 32 further has a central aperture 46 in which a window 48 is seal-fitted to define the rest of the second side of sample-holding volume 30 as a continuation of outer surface 34. Window 48 is formed of a material which is substantially transparent at the wavelength of electrochemiluminescent light emitted by the ECL moiety. Window 48 is therefore advantageously formed of glass, plastic, quartz or the like.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12.

Mounted on inner surface 28 of first mounting block 20 is a working electrode system 54 which, in the illustrated embodiment, includes first and second working electrodes 56 and 58. In other embodiments, a single working electrode may advantageously be provided, or only electrode 56 may be a working electrode. Working electrodes 56, 58 are where the electrochemical and ECL reactions of interest can take place. Working electrodes 56, 58 are solid voltammetric electrodes and may therefore be advantageously constructed of platinum, gold, carbons or other materials which are effective for this purpose. Wire connectors 60, 62 connected to working electrodes 56, 58, respectively, pass out through first mounting block 20.

Connectors 60, 62 are both connected to a first, "working electrode" terminal 64 of a voltage control 66, illustrated in FIG. 2. Voltage control 66 advantageously operates in the manner of a potentiostat to supply voltage signals to working electrodes 56, 58 and optionally to measure current flowing therefrom during an ECL measurement. Alternatively, connectors 60, 62 may be connected to separate terminals of voltage control 66 for individual operation.

The potentiostat operation of voltage control 66 is further effected through a counter electrode 68 and, optionally but advantageously, a reference electrode 70. In the illustrated embodiment, mounting block 32 is made of stainless steel and counter electrode 68 consists in exposed surfaces 72, 74 of mounting block 32. Counter electrode 72, 74 and working electrodes 56, 58 provide the interface to impress the potential on the solution within sample-holding volume 30 which energizes the chemical reactions and triggers electrochemiluminescence in the sample and/or provides energy for cleaning and conditioning the surfaces of cell 12. Counter electrode 72, 74 is connected by a wire connector 76 to a second, "counter electrode" terminal 78 of voltage control 66.

Reference electrode 70 provides a reference voltage to which the voltage applied by the working electrodes 56, 58 is referred, for example, +1.2 volts versus the reference. Reference electrode 70 is advantageously located in outlet tube 24 at a position 80 spaced from cell 12 and is connected through a wire connector 82 to a third "reference electrode" terminal 84 of voltage control 66. In the three electrode mode, current does not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 may be operable in a two electrode mode of operation using only working electrode 56 and electrode 58 as a counter/reference electrode. In this two electrode mode of operation, counter/reference electrode 58 is electrically connected to voltage control terminals 78 and 84 on voltage control 66. In this case, voltage control 66 operates essentially as a battery. Voltage control 66 supplies voltage signals to working and counter electrodes 56 and 58 and optionally measures the current flowing through the respective electrodes. Reference electrode 70 may alternatively be a so-called "quasi-reference" electrode constructed of platinum, gold, stainless steel or other material, which provides a less stable voltage, yet one that is measurable with respect to the solution in contact. In both the two and three electrode mode, the reference electrode 70 or 58 serves the purpose of providing a reference against which the voltage applied to working electrodes 56 is measured. The poised voltage reference is currently considered to be more advantageous. Voltage control 66 in its potentiostat operation controls the various electrodes by providing a known voltage at working electrodes 56, 58 with respect to reference electrode 70 while measuring the current flow between working electrodes 56, 58 and counter electrode 72, 74. Potentiostats for this purpose are well known, and the internal structure of voltage control 66 may therefore correspond to any of the conventional, commercially available potentiostats which produce the above-recited functions and so do not form a part of the present invention per se. Indeed, apparatus 10 may alternatively be constructed without an internal voltage control 66, and may be adapted to be connected to an external potentiostat which is separately controlled for providing the required voltage signals to electrodes 56, 58, 72, 74 and 70. These voltage signals, applied in a specific manner as described below, provide repeatable initial conditions for the surfaces of working electrodes 56, 58 and advantageously for the surfaces of cell 12 as a whole, a feature which contributes significantly to improved precision in ECL measurements.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 past reference electrode 70 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

The flow-through construction of apparatus 10 permits working electrodes to be impressed with a variable voltage or to be continuously held at a preoperative potential while being continuously exposed to one or more solutions without exposing working electrodes 56, 58 (or counter and reference electrodes 72, 74, 70) to air. Exposure to air, which opens the circuit to the reference electrode 70, permits unknown, random voltage fluctuations which destroy the reproducibility of surface conditions on working electrodes 56, 58. The flow-through construction permits the rapid alternation between initializing steps, in which electrode system 54 is cleaned and conditioned, and measurement steps, in which one or more measurement waveforms or sweeps trigger ECL.

The invention is also directed to reagent compositions. Broadly, the reagent compositions may be any one of the components of the assay systems of the invention, i.e., (a) electrolyte, (b) label compound containing an ECL moiety, (c) particles, (d) analyte of interest or an analog of the analyte of interest, (e) a binding partner of the analyte of interest or of its analog, (f) a reactive component capable of reacting with (d) or (e), (g) a reductant, or (h) an electrochemiluminescent-reaction enhancer. The reagents may be combined with one another for convenience of use, i.e., two component, three component, and higher multiple component mixtures may be prepared, provided that the components are not reactive with one another during storage so as to impair their function in the intended assay. Desirably, the reagents are two-component or multicomponent mixtures which contain particles as well as one or more other components.

The invention is also directed to kits for use in microparticulate-based nonseparation binding assays. The kits may include vessels containing one or more of the components (a) to (h) recited above or the kits may contain vessels containing one or more reagent compositions as described above comprising mixtures of those components, all for use in the assay methods and systems of the invention.

A preferred kit for hybridoma screening may include, for example:

(1) a buffer, as more particularly described in the following examples, (2) a label compound in concentrated form, and (3) particles which are capable of coupling to an antigen of interest in the intended assay system or which are capable of coupling to a component of the intended assay system.

The methods of the invention are further described in the following examples. The invention is not limited to antigen-antibody reactions as exemplified but can be used to carry out other binding reactions, for example, RNA-DNA hybridizations and receptor-ligand interactions.

EXAMPLES

Instrumentation, Materials, and Methods (1) Instrumentation

A flow-through apparatus, employing three electrodes, as described in FIGS. 1 and 2, was used.

Working Electrode—both Au disks

Counter Electrode—stainless steel faceplate

Reference Electrode—Ag/AgCl

Teflon Gasket (0.15" thick)

Stainless Steel/Plexiglas Faceplate

Inlet Tubing=0.042" id polypropylene

Aspiration Rates 2 ml/min

Potentiostat: Oxford

Luminometer:

Berthold Biolumat LB9500 T (photon counting)

PMT=Hamamatsu R374 (low gain red sensitive tube)

PMT Voltage =+1350V

The current and photon output were recorded on a Kipp & Zonen recorder.

(2) Materials (a) TAG: Tris(2,2'-bipyridyl)-ruthenium(II)

(b) BioMag$^{(R)}$ (Exs. 1, 2, 4, 5, 6, and 7):

BioMag 4100, a suspension of black, magnetic iron oxide particles coated to provide primary amino groups. The amino groups are stearically unencumbered, permitting the covalent attachment of proteins or ligands with the retention of biological activity. BioMag$^{(R)}$ was obtained from Advanced Magnetics Inc., 61 Mooney Street, Cambridge, Mass. 02138.

(c)

(i) ECL buffer (Exs. 1, 2, and 4):

75 mM potassium phosphate buffer pH 7.24 containing 100 mM tripropylamine (TPA) and 0.05% Tween-20 (a nonionic surfactant);

(ii) ECL buffer (Ex. 3):

75 mM potassium phosphate buffer pH 7.24 containing 100 mM tripropylamine (TPA), 0.1% Triton X-100 (nonionic surfactant), and 0.05% Tween-20 (nonionic surfactant);

(iii) ECL buffer (Exs. 5, 6, and 7):

150 mM potassium phosphate solution 50 mM tripropyl amine pH adjusted to 7.5 with NaOH (50%) 0.05% Triton X-100 (TM) (nonionic surfactant) 0.05% Tween-20 (TM) (nonionic surfactant) water added to make 2.0 liter;

(d) polystyrene latex particles:

Pandex carboxylated particles 5% w/v obtained from Pandex Laboratories, Inc., 909 Orchard Street, Mundelein, Ill. 60060 (Cat. No. 31-010-1);

(e) Hybridoma Growth Media (HGM):

a diluted and modified form of Iscove's Modified Dulbecco's Media (IMDM), obtained from J.R. Scientific, Inc., One Harter Avenue, Suite 8, Woodland, Calif. 95695. See, Dulbecco, R., and Freeman, G., (1959) *Virology* 8, 398; Smith, J. D., Freeman, G., Vogt, M., and Dulbecco, R., (1960) *Virology* 12, 155; Tissue Culture Standards Committee, *In Vitro* 5:2, 93, and Iscove, N. N., and Melchers, F., *J. Experimental Medicine* 147, 923. 100% HGM contains 200 ml IMDM (JR Scientific lot C077201), 40 ml fetal bovine serum (batch 67, HI), 2 ml 5×10$^{-3}$ M 2-mercaptoethanol (batch 39), 2 ml kanamycin sulfate (10,000 mg/ml, lot 13N2672, 4 ml HAT (10$^{-2}$M hypoxanthine, 4×10$^{-5}$M aminopterin, 1.6×10-3 M thymidine; stock GIBCO), 40 ml 1° MCM primary microphage conditioning media(Nov. 7, 1986, harvest 4). It is diluted to 1 part in 20 with buffer solution to prepare 5% HGM.

(3) Methods (a) Coating BioMag (Exs. 1, 2, 5, 6, 7):

By art-known procedures, e.g., methods for covalently attaching proteins by reagents used to prepare affinity supports, provided that the solid phase terminates with a primary amine group. A glutaraldehyde procedure is given in Weston and Avramers (Biochem. Biophy. Res. Comm. 45, 1574 (1971)).

(b) Coating Polylstyrene Latex (Ex. 3):

By art-known procedures, e.g., mixing particles and bovine serum albumin (BSA), incubating, centrifuging, and decanting.

(c) preparation of digoxin-bovine thyroglobulin:

By the method disclosed in Freytag et al., Clin. Chem. 30/9 1494–1498 (1984).

(d) Linking TAG to proteins and digoxin:

By art-known methods using aldehyde linkages or N-hydroxy succinamide ester linkages as taught, e.g., in parent application, PCT US87/00987.

(4) ECL Measurement Cycle (three electrode cell operation) Cleaning/Conditioning/Sample Measurement Procedure:

The total cycle used in obtaining this data included 6 steps, each step using the same applied voltage waveform. Each cycle had two conditioning steps (with the solution flowing), one sample measurement step (with the measurement solution flowing or stagnant), two cleaning steps followed by one conditioning step (with the conditioning solution flowing). Each step used the following applied voltage sweep at a constant 500 mV/sec for the electrochemical cycle:

+0.3V to −0.7V to +2.2V and back to +0.3V. Sample volume was 1.0 ml.

Competition Assays

The microparticulate-based nonseparation binding assay can be used in a luminescent intensity modulation immunoassay competition format. The substance linked to the label compound is added analyte of interest. The binding partner is bound to the particles and the particles are therefore capable of specifically binding with the analyte of interest or the labeled added analyte of interest. The analyte of interest and the added analyte of interest may be an antigen.

Alternatively, the binding partner may be a primary binding partner of the analyte of interest. A secondary binding partner of the primary binding partner is bound to the particles and accordingly the particles are capable of specifically binding with the primary binding partner. The assay mixture contains the analyte of interest, the labeled added analyte of interest and the primary binding partner. The analyte of interest and the added analyte of interest may be antigens.

Small analytes of interest such as theophylline may be determined as in Example 1 or large analytes of interest such as human IgG may be determined as in Example 2.

Example 1

A microparticulate-based nonseparation competitive binding assay for the determination of theophylline was conducted as follows:

reagents:

(1) theophylline standards: 0, 2.5, 5, 10, 20, 40 ug/ml;
(2) theophylline tracer (100 nM) (theophylline-8-butyric acid linked to TAG);
(3) anti-theophylline monoclonal antibody covalently coupled to BioMag$^{(R)}$ (magnetic particles) 1% suspension wt/vol);
(4) ECL buffer.

A series of tubes (12×75 mm polypropylene) were set up and labeled according to standards to be assayed. Into each tube was added 920 ul of ECL buffer, 10 ul of respective standards or samples, 20 ul of anti-theophylline-BioMag$^{(R)}$ and 50 ul of diluted theophylline tracer. Tubes were mixed and incubated at room temperature for 10 minutes. Electrochemiluminescence was read in the flow-through ECL instrument. The results were as follows:

| Theophylline Concentration ug/ml | ECL Units (after background NSB subtraction) | % of Total ECL Counts |
| --- | --- | --- |
| 0.0 | 5050 | 31.7 |
| 2.5 | 6500 | 40.8 |
| 5.0 | 7450 | 46.7 |
| 10.0 | 8800 | 55.2 |
| 20.0 | 10,750 | 67.4 |
| 40.0 | 12,650 | 79.3 |

Example 2

A microparticulate-based nonseparation binding assay to determine human IgG was prepared having the following components:

(1) human IgG standards: 2, 20, and 200 ug/ml;
(2) goat anti-human IgG covalently coupled to BioMag$^{(R)}$ particles (1% suspension wt/vol);
(3) TAG-labeled human IgG diluted to 1/160 of stock in ECL buffer;
(4) ECL buffer: 75 mM potassium phosphate buffer at pH 7.24 containing 100 mM tripropylamine (TPA) and 0.05% Tween-20;
(5) goat anti-rabbit IgG covalently coupled to BioMag$^{(R)}$ (1% suspension) for nonspecific binding determination.

A series of tubes (12×75 mm polypropylene) were set up and labeled according to standards to be assayed. Into each tube was added 100 ul of TAG-human IgG and 100 ul of the respective human IgG standard (0 to 200 ug/ml). A 50 ul aliquot of goat anti-human IgG-BioMag$^{(R)}$ and a 750 ul aliquot of ECL buffer was then added to each tube followed by vortexing and a 20 min room temperature incubation with agitation. For the nonspecific binding (NSB) study, goat anti-rabbit IgG-BioMag$^{(R)}$ particles were substituted for the anti-human IgG particles.

ECL was read by normal flow-through protocol at a gold working electrode. The results were as follows:

| Human IgG ug/ml | % of Total ECL Counts |
| --- | --- |
| 0 | 35.4 |
| 0.2 | 38.7 |
| 2.0 | 57.5 |
| 20.0 | 81.0 |
| NSB | 100.0 |

Example 3

A microparticulate-based nonseparation binding assay to determine mouse IgG was conducted using the following components:

(1) mouse IgG standards: 4, 20, and 200 ug/ml;
(2) goat anti-mouse IgG covalently coupled to polystyrene latex particles (0.5% suspension wt/vol);
(3) TAG-labeled mouse IgG diluted to 1/2600 of stock in ECL buffer;
(4) ECL buffer;
(5) BSA-polystyrene latex particles (0.5% suspension) for nonspecific binding determination.

A series of tubes (12×75 mm polypropylene) were set up and labeled according to standards to be assayed. Each tube received 900 ul of TAG-mouse IgG solution and 50 ul of the respective mouse IgG standards. Either 50 ul of goat anti-mouse IgG-latex or BSA-latex was added to the tubes to initiate the immunoreaction. The tubes were incubated for 25 min at room temperature without agitation.

ECL of the suspensions was read according to normal flow-through protocol.

The results were as follows:

| Mouse IgG ug/ml | ECL Counts | % of Total |
| --- | --- | --- |
| 0 | 2,695 | 46 |
| 0.2 | 3,045 | 51 |
| 1.0 | 4,745 | 80 |
| 10 | 5,895 | 99 |
| Total | 5,920 | 100 |
| NSB | 6,195 | 104 |

Immunometric Assays

The microparticulate-based nonseparation binding assay can be used in an immunometric format. The substance linked to the label compound is a binding partner of the analyte of interest. The analyte or an analog thereof is bound to the surface of the particles and accordingly the particles are capable of specifically binding with the binding partner. The analyte of interest may be an antigen.

Alternatively, the binding partner is a primary binding partner of the analyte of interest. A binding partner of the primary binding partner is the substance linked to the label compound. Analyte or an analog thereof is bound to the surface of the particles and accordingly the particles are capable of specifically binding with the primary binding partner. The secondary binding partner linked to the label compound specifically binds the primary binding partner. The analyte of interest may be an antigen.

Example 4

A microparticulate-based nonseparation binding assay to determine digoxin was prepared having the following components:

(1) digoxin standards: 1.0, 5.0, 10, 100, and 250 ng/ml;
(2) digoxin-bovine thyroglobulin covalently coupled to BioMag(R) particles (1% suspension wt/vol);
(3) TAG-labeled anti-digoxin monoclonal antibody diluted to 1/150 of stock in ECL buffer;
(4) ECL buffer;
(5) goat anti-rabbit IgG-Biomag(R) (1% suspension) for nonspecific binding determination.

A series of tubes (12×75 mm polypropylene) were set up and labeled according to standards to be assayed. Each tube received 100 ul of the respective digoxin standard and 100 ul of TAG-anti-digoxin conjugate. The tubes were allowed to incubate for 25 min at room temperature with agitation followed by the addition of 50 ul of either digoxin-BTG-BioMag(R) or goat anti-rabbit IgG-BioMag(R) and further incubated for 10 min at room temperature with agitation. The volume was adjusted to 1 ml and ECL of the suspension was read according to normal flow-through protocol.

| Digoxin ng/ml | ECL Counts | % of Total |
|---|---|---|
| 0 | 2,150 | 32.1 |
| 0.1 | 2,250 | 33.6 |
| 0.5 | 2,500 | 37.3 |
| 1.0 | 2,950 | 44.0 |
| 10 | 4,700 | 70.1 |
| 25 | 6,800 | 102 |
| Total | 6,700 | 100 |
| NSB | 7,000 | 103 |

Sandwich Assays

The microparticulate-based nonseparation binding assay can be used in a sandwich assay format. The analyte of interest may be an antigen. The substance linked to the label compound is a binding partner of the analyte of interest. A binding partner not linked to the label compound is also bound to the surface of the particles and accordingly they are capable of binding to the analyte of interest.

Alternatively, the binding partner may be a primary binding partner (BP-1) of the analyte of interest. A secondary binding partner of the primary binding partner is the substance linked to the label compound. The analyte of interest may be an antigen. Another primary binding partner (BP-2) which is not recognized by the secondary binding partner is bound to the surface of the particles and accordingly they are capable of binding to the analyte of interest. The particles and primary binding partner (BP-1) are capable of specifically binding the antigen and the secondary binding partner linked to the label compound is capable of specifically binding the primary binding partner (BP-1).

Alternatively, the binding partner may be a primary binding partner (BP-1) of the analyte of interest. BP-1 is linked to the label compound. Another primary binding partner (BP-1') which is different from BP-1 and binds the analyte of interest is used. A secondary binding partner of the primary binding partner BP-1' is bound to the surface particles and accordingly they are capable of binding the complex of analyte, BP-1 and BP-1'.

Example 5

A microparticulate-based nonseparation binding assay to determine mouse $IgG_{2a}$ was prepared having the following components:

(1) mouse $IgG_{2a}$ standards: 10, 40, 160, 625, 2500, 10,000, and 50,000 ng/ml in hybridoma growth media;
(2) goat anti-mouse IgG (Fc specific) covalently coupled to BioMag(R) particles (1% suspension wt/vol);
(3) TAG-labeled goat anti-mouse IgG (heavy and light chain specific) 150 ng/ml in ECL buffer;
(4) ECL buffer;
(5) BSA covalently coupled to BioMag(R) particles (1% suspension wt/vol) for NSB determination.

A series of tubes (12×75 mm polypropylene) were set up and labeled according to the standards to be assayed. Into each tube 100 ul of the respective standard, 500 ul of TAG goat anti-mouse reagent, 300 ul of ECL assay buffer, and 100 ul of the respective BioMag(R) particle reagent, were combined. The tubes were allowed to incubate for 15 min at room temperature. Electrochemiluminescence was read according to the previously described procedure.

The results were as follows:

| Mouse $IgG_{2a}$ Concentration ng/ml | ECL Readings Specific Binding | % of Modulation | Nonspecific Binding |
|---|---|---|---|
| 0 | 2112 | 0 | 2142 |
| 1 | 2076 | 1.8 | 2102 |
| 4 | 1992 | 6.1 | 2088 |
| 16 | 1836 | 14 | 2076 |
| 63 | 1608 | 26 | 2064 |
| 250 | 1392 | 37 | 2052 |
| 1000 | 1200 | 47 | 2040 |
| 5000 | 1140 | 50 | 2040 |
| Blank | 140 | 100 | |

$$\% \text{ Modulation} = \frac{1 - (ECL_o - ECL_{blank}) - (ECL_x - ECL_{blank}) \times 100\%}{(ECL_o - ECL_{blank})}$$

$$= \left(1 - \frac{ECL_x - ECL \text{ blank}}{ECL_o - ECL \text{ blank}}\right) \times 100\%$$

Hybridoma Screening Assays

The microparticulate-based nonseparation binding assay can be used in a hybridoma screening assay format. The analyte of interest is a monoclonal antibody directed against a particular antigen. The substance linked to the label compound is a binding partner of the analyte of interest. Antigen is bound to the surface of the particles and accordingly they are capable of specifically binding with the analyte. The monoclonal antibody specifically binds the particles and the binding partner linked to the label compound specifically binds the monoclonal antibody.

Advantageously, the labeled binding partner capable of specifically binding the monoclonal antibody is a polyclonal antibody, a monoclonal antibody, protein A, or protein G. In addition, the labeled binding partner may be avidin, which can bind to a biotin-modified analyte or binding partner.

Alternatively, the binding partner may be a primary binding partner of the analyte of interest. A binding partner of the primary binding partner is the substance linked to the label compound. The analyte of interest is a monoclonal antibody directed against an antigen. Antigen is bound to the surface of the particles and accordingly they are capable of specifically binding with the monoclonal antibody. The monoclonal antibody specifically binds the particles, the primary binding partner specifically binds the monoclonal antibody, and the secondary binding partner linked to the label compound specifically binds the primary binding partner.

Example 6

A microparticulate-based, nonseparation, binding, sandwich assay (hybridoma screening assay format) for the detection of monoclonal antibodies to digoxin was conducted as follows:

reagents:
(1) goat anti-mouse IgG covalently linked to TAG;
(2) (a) digoxin-BSA, and (b) BSA covalently coupled to BioMag$^{(R)}$ particles for detecting specific antibodies and nonspecific binding antibodies, respectively;
(3) hydridoma growth media sample suspected of containing monoclonal anti-digoxin antibodies, or, for reference purposes containing a known amount of antibodies ranging from 1 to 50 ug/ml in hybridoma culture media;
(4) ECL buffer.

A series of tubes were set up (12×75 mm polypropylene) and labeled according to sample number or sample containing known amounts of monoclonal antibodies to digoxin. To each tube was added 50 ul of hybridoma supernatant suspected of containing antibodies to digoxin, 50 ul of digoxin-BSA coupled to BioMag$^{(R)}$ and 100 ul of diluted goat anti-mouse IgG TAG (1 ug/ml) and the volume was adjusted to 1 ml by adding 800 ul of ECL buffer. The tubes were vortexed and incubated at room temperature for 15 minutes with agitation. For the non specific binding study, BSA-BioMag particles were added instead of digoxin-BSA particles. The electrochemiluminescence of the suspension was measured in a flow-through mode. The results were as follows:

| Anti-digoxin Antibody | ECL Readings | | |
|---|---|---|---|
| Concentration ug/ml | Specific Binding | % of Total | Nonspecific Binding |
| 0 | 2537 | 100 | 2597 |
| .06 | 2107 | 81 | 2524 |
| .31 | 1680 | 64 | 2520 |
| .63 | 1536 | 58 | 2490 |
| 1.25 | 1428 | 53 | 2513 |
| 2.50 | 1380 | 51 | 2448 |

Example 7

A microparticulate-based nonseparation hybridoma screening method for the detection of monoclonal antibodies to human IgG was conducted as follows:

reagents:
(1) human IgG covalently coupled to BioMag$^{(R)}$ magnetic particles (1%) suspended in 0.1M PBS containing thiomersal and BSA;
(2) goat anti-mouse IgG linked to TAG diluted to 1 ug/ml in ECL assay buffer just before use;
(3) hybridoma culture supernatant containing various amounts of monoclonal antibody to human IgG (0 to 12,000 ng/ml);
(4) ECL buffer;
(5) goat IgG coupled to BioMag$^{(R)}$ particles for nonspecific binding determination.

A series of polypropylene tubes (12×75 mm) was set up and labeled according to standards to be assayed. 100 ul of hybridoma supernatant containing various concentrations of mouse anti-human antibodies; 50 ul of BioMag$^{(R)}$ particles (1% solids) with immobilized human IgG, 100 ul of goat anti-mouse-TAG (diluted) and 750 ul of ECL buffer. For nonspecific determination, 50 ul of BioMag$^{(R)}$ particles with immobilized goat IgG was used instead of human IgG. The tubes were mixed, incubated at room temperature for 15 minutes and the electrochemiluminescence was read as described above. The following results were obtained.

| Anti-human IgG Antibody | ECL Readings | | |
|---|---|---|---|
| Concentration ng/ml | Specific Binding | % of Total | Nonspecific Binding |
| 0.0 | 1692 | 100 | 1668 |
| 13 | 1704 | 101 | 1716 |
| 63 | 1596 | 93 | 1752 |
| 125 | 1500 | 87 | 1704 |
| 250 | 1404 | 81 | 1752 |
| 500 | 1284 | 73 | 1716 |
| 1,000 | 1154 | 64 | 1704 |
| 3,000 | 1042 | 58 | 1680 |
| 6,000 | 969 | 53 | 1728 |
| 12,000 | 909 | 49 | 1716 |

The data obtained in the Examples demonstrate that calibration curves can be drawn over a wide range of analyte concentrations and that sensitive analyses can be made over the entire range of concentrations in actual samples.

What is claimed is:

1. A method for the detection or quantitation of an analyte of interest in a sample, which method comprises the steps of:
   (1) forming a composition comprising:
      (a) a sample, which may comprise a first quantity of the analyte of interest;
      (b) at least one reagent substance selected from the group consisting of:
         (i) a second quantity of the analyte of interest or an analog of the analyte of interest, and
         (ii) a binding partner of the analyte of interest or its said analog,
         wherein one of said reagent substances is linked to a label compound capable of being induced to electrochemiluminesce; and
      (c) a second reagent comprising a plurality of particles which are: (i) capable of specifically binding with the analyte of interest or (ii) attached to the second quantity of the analyte of interest or its analog, wherein said particles and said analyte are different;
   (2) inducing the label compound to electrochemiluminesce; and
   (3) measuring luminescence emitted by the label compound to determine whether or not, or in what amount, the analyte of interest is present in the sample.

2. A method according to claim 1, wherein the particles comprise:
   (a) microparticulate matter having a diameter of from 0.01 μm to 200 μm, and (b) a surface component capable of specifically binding to the analyte and/or at least one reagent substance defined in (b)(i) or (b)(ii).

3. A method according to claim 2, wherein the microparticulate matter is selected from the group consisting of crosslinked starch, dextrans, cellulose, organic polymers, styrene copolymer, inert organic particles, proteinaceous matter and combinations thereof.

4. A method for the detection and quantitation of an analyte of interest in a sample, which method comprises the steps of:
   (1) forming a composition comprising:
      (a) a sample, which may comprise a first quantity of the analyte of interest;
      (b) a known amount of at least one reagent substance selected from the group consisting of:
         (i) a second quantity of the analyte of interest or an analog of the analyte of interest, and
         (ii) a binding partner of the analyte of interest or its said analog,
         wherein one of said reagent substances is linked to a label compound capable of being induced to electrochemiluminesce, and
      (c) a known amount of a second reagent comprising particles which are: (i) capable of specifically binding with the analyte of interest or (ii) attached to the second quantity of the analyte of interest or its analog, wherein said particles and said analyte are different;
   (2) inducing the label compound to electrochemiluminesce; and
   (3) comparing the luminescence emitted by the label compound to the luminescence of a calibration standard to determine whether or not, or in what amount, the analyte of interest is present in the sample.

5. A method according to claim 4, wherein the particles comprise
   (a) microparticulate matter having a diameter of from 0.01 µm to 200 µm, and
   (b) a surface component capable of specifically binding to the analyte and/or at least one reagent substance defined in (b)(i) or (b)(ii).

6. A method according to claim 5, wherein the microparticulate matter is selected from the group consisting of crosslinked starch, dextrans, cellulose, organic polymers, acrylamides, polystyrene, polybutadiene, inert inorganic particles, proteinaceous matter and combinations thereof.

7. A method as recited in claim 1 or 4, wherein the reagent substance recited in (b) includes a primary binding partner of the analyte of interest and a secondary binding partner linked to the label compound.

8. A method as recited in claim 7, wherein the analyte of interest is a monoclonal antibody and both the particles and the primary binding partner are capable of specifically binding with the monoclonal antibody, and wherein during the assay the monoclonal antibody becomes specifically bound to the particles, the primary binding partner becomes specifically bound to the monoclonal antibody, and the secondary binding partner linked to the label compound becomes specifically bound to the primary binding partner.

9. A method as recited in claim 7, wherein the particles are capable of specifically binding with the primary binding partner and the secondary binding partner linked to the label compound specifically binds the primary binding partner.

10. A method as recited in claim 9, wherein the analyte of interest is an antigen, the particles contain the antigen or an analog of the antigen, and the primary binding partner is capable of specifically binding the antigen and its analog.

11. A method as recited in claim 7, wherein the analyte of interest is an antigen, the particles and the primary binding partner are capable of specifically binding the antigen and the secondary binding partner linked to the label compound is capable of specifically binding the primary binding partner.

12. A method as recited in claim 1 or 4, wherein the reagent substance linked to the label compound is the binding partner of the analyte of interest and the particles are capable of specifically binding with the analyte.

13. A sandwich method as recited in claim 12, wherein the analyte of interest is an antigen, and the particles and the binding partner are capable of specifically binding the antigen.

14. A method as recited in claim 12, wherein the analyte of interest is a monoclonal antibody and the particles and the binding partner are both capable of specifically binding with the monoclonal antibody, and wherein during the assay the monoclonal antibody becomes specifically bound to the particles and the binding partner that has been linked to the label compound becomes specifically bound to the monoclonal antibody.

15. A method as recited in claim 1 or 4, wherein the reagent substance linked to the label compound is the binding partner of the analyte of interest and the particles are capable of specifically binding with the binding partner.

16. A method as recited in claim 15, wherein the analyte of interest is an antigen, the surface of the particles contains the antigen or an analog of the antigen, and the binding partner is capable of specifically binding the antigen or its analog.

17. A method as recited in claim 1 or 4, wherein the method is a competitive assay and the reagent linked to the label compound is added analyte of interest and wherein the particles are capable of specifically binding with the analyte of interest or the added analyte of interest.

18. A method as recited in claim 17, wherein the analyte of interest is an antigen and the particles are capable of specifically binding the antigen.

19. A method as recited in claim 1 or 4, wherein the assay mixture contains added analyte of interest and a binding partner of the analyte of interest, and wherein the reagent substance linked to the label compound is added analyte of interest and the particles are capable of specifically binding with said binding partner.

20. A method as recited in claim 19, wherein the analyte of interest and the added analyte of interest is an antigen, the binding partner is capable of specifically binding the antigen and the particles are capable of specifically binding the binding partner.

21. The method of claim 1 or 4, wherein said luminescence is measured in the presence of said particles.

22. An assay method for determining the presence or amount of an analyte of interest based upon a specific binding reaction and the measurement of an electrochemiluminescent phenomenon comprising the steps of:
   (a) forming an assay mixture containing:
      (i) a sample containing a first quantity of the analyte of interest,
      (ii) at least one reagent substance selected from the group consisting of
         (A) a second quantity of the analyte of interest or an analog of the analyte of interest, and
         (B) a binding partner of the analyte of interest or its said analog,
         wherein one of said reagent substances is linked to a label compound having a chemical moiety capable of being induced to electrochemiluminesce, and (iii) a second reagent comprising a plurality of inanimate particles which are: (1) capable of specifically binding with the analyte of interest and/or (2) attached to the second quantity of the analyte or its analog; and (b) incubating said assay mixture to permit binding;

(c) causing the label compound to electrochemiluminesce; and (d) measuring electrochemiluminescence emitted by said label compound and correlating said measurement to a calibration standard to determine whether or not, or in what amount the analyte of interest is present in the sample.

23. A method according to claim 21, wherein prior to step (b) any reagent which is not combined with the analyte of interest is separated from the sample resulting from step (a).

24. A homogeneous assay method for determining the presence or amount of an analyte of interest based upon a specific binding reaction and the measurement of an electrochemiluminescent phenomenon comprising the steps of:

(a) forming an assay mixture containing:
  (i) a sample containing a first quantity of the analyte of interest,
  (ii) at least one reagent substance selected from the group consisting of:
    (A) a second quantity of the analyte of interest or an analog of the analyte of interest, and
    (B) a binding partner of the analyte of interest or its said analog,
    wherein one of said reagent substances is linked to a label compound having a chemical moiety capable of being induced to electrochemiluminesce; and
  (iii) a second reagent comprising a plurality of particles which are: (A) capable of specifically binding with the analyte and/or (B) attached to the second quantity of the analyte of interest or its analog, wherein said particles and said analyte are different; and (b) introducing said assay mixture into an electrochemiluminescence cell;

(c) causing the label compound to electrochemiluminesce in said electrochemiluminescence cell; and (d) measuring electrochemiluminescence emitted by said label compound in the presence of said particles in said electrochemiluminescence cell and correlating said measurement to a calibration standard to determine whether or not, or in what amount, the analyte of interest is present in the sample.

25. An assay method for determining the presence or amount of an analyte of interest based upon a specific binding reaction and the measurement of an electrochemiluminescent phenomenon comprising the steps of:

(a) forming an assay mixture containing:
  (i) a sample containing a first quantity of the analyte of interest,
  (ii) at least one reagent substance selected from the group consisting of:
    (A) a second quantity of the analyte of interest or an analog of the analyte of interest, and
    (B) a binding partner of the analyte of interest or its said analog,
    wherein one of said reagent substances is linked to a label compound having a chemical moiety capable of being induced to electrochemiluminesce; and
  (iii) a second reagent comprising a plurality of inanimate particles which are: (A) capable of specifically binding with the analyte or (B) attached to the second quantity of the analyte of interest or its analog;

(b) introducing said assay mixture into an electrochemiluminescence cell;

(c) causing the label compound to electrochemiluminesce in said electrochemiluminescence cell; and (d) measuring electrochemiluminescence emitted by said label compound in said electrochemiluminescence cell and correlating said measurement to a calibration standard to determine whether or not, or in what amount, the analyte of interest is present in the sample.

26. An assay composition for use in detecting an analyte of interest in a sample, comprising:

(a) a sample containing the analyte of interest, (b) at least one reagent substance selected from the group consisting of
  (i) added analyte of interest or an analog of the analyte of interest,
  (ii) a binding partner of the analyte of interest or its said analog, and
  (iii) a reactive component capable of binding with (i) or (ii), wherein one of said reagent substances is linked to a label compound having a chemical moiety capable of being induced to electrochemiluminesce, (c) a second reagent comprising a plurality of inanimate particles capable of specifically binding with the analyte and/or at least one reagent substance defined in (b)(i), (b)(ii), or (b)(iii), and (d) a reductant that under oxidizing conditions interacts with the label compound to generate electrochemiluminescence.

27. An assay composition as recited in claim 26 further containing an electrolyte adapted to facilitate electrochemiluminescences.

28. A composition as recited in claim 27 wherein said particles are suspended in the assay composition.

29. The composition of claim 26, wherein said composition is in an electrochemiluminescent cell.

30. A composition of matter for use as a reagent in a microparticulate-based electrochemiluminescence binding assay for determining the presence or amount of an analyte of interest, comprising (i) a reagent comprising microparticles which are capable of binding with said analyte of interest or linked to said analyte of interest or its analog, (ii) a label containing an ECL moiety, (iii) a reductant that under oxidizing conditions interacts with the label compound to generate electrochemiluminescence and (iv) at least one other assay component selected from the group consisting of:

(a) electrolyte, (b) analyte of interest or an analog of the analyte of interest, (c) a binding partner of the analyte of interest or its analog, (d) a reactive component capable of reacting with (b) or (c), and (e) an electrochemiluminescent-reaction enhancer, provided, however, that no two components contained within said composition are reactive with one another during storage so as to impair their function in the intended assay and said composition is suitable for use in said microparticulate-based electrochemiluminescence binding assay.

31. An assay reagent as recited in claim 30 wherein three components are present in said reagent.

32. The composition of matter of claim 30, wherein said microparticles are selected from the group consisting of polymeric particles, inorganic particles, metallic particles, metal oxide particles, composite particles and mixtures thereof.

33. The composition of matter of claim 30, wherein said microparticles have a diameter of 0.5 μm to 10 μm.

34. The composition of matter of claim 30, wherein said analyte of interest and said microparticles are different.

35. The composition of claim 30 wherein said composition is in an electrochemiluminescent cell.

36. A kit containing in one or more vessels reagents for use in a microparticulate-based electrochemiluminescence binding assay for determining the presence or amount of an analyte of interest comprising:
  (1) a label compound reagent containing an ECL moiety,
  (2) a reagent comprising microparticles which are: (i) capable of binding with said analyte of interest or a reactive component capable of binding with said analyte of interest or (ii) linked to said analyte of interest or its analog, and
  (3) at least one other assay reagent component selected from the group consisting of:
    (a) electrolyte,
    (b) analyte of interest or an analog of the analyte of interest,
    (c) a binding partner of the analyte of interest or its analog,
    (d) a reactive component capable of reacting with (b) or (c),
    (e) a reductant that under oxidizing conditions interacts with the label compound to generate electrochemiluminescence, and
    (f) an electrochemiluminescent reaction enhancer;
provided, however, that no two of said reagents react with one another under storage conditions so as to impair the function of the reagents in the intended assay, and wherein said kit is suitable for use in said microparticle-based electrochemiluminescence binding assay.

37. The kit of claim 36, wherein at least one other assay reagent component comprises said reductant.

38. The kit of claim 36, wherein said particles are selected from the group consisting of polymeric particles, inorganic particles, metallic particles, metal oxide particles, composite particles and mixtures thereof.

39. The kit of claim 36, wherein said microparticles have a diameter of 0.5 μm to 10 μm.

40. The kit of claim 36, wherein said analyte of interest and said microparticles are different.

41. The kit of claim 36, wherein said microparticles are capable of binding with said binding partner of said analyte of interest and said composition further comprises said binding partner of said analyte of interest.

42. A system for detecting or quantitating an analyte of interest in a sample based upon an electrochemiluminescent phenomenon comprising:
  (a) a sample;
  (b) at least one reagent substance selected from the group consisting of
    (i) added analyte of interest or an analog of the analyte of interest,
    (ii) a binding partner of the analyte of interest or its said analog, and
    (iii) a reactive component capable of binding with (i) or (ii), wherein one of said reagent substances is linked to a label compound having a chemical moiety capable of being induced to electrochemiluminesce;
  (c) a reagent comprising (i) a plurality of particles capable of specifically binding to the analyte or (ii) a plurality of particles linked to said analyte or its analog;
  (d) a reductant that under oxidizing conditions interacts with the label compound to generate electrochemiluminescence;
  (e) a voltage source for inducing the label compound to electrochemiluminesce; and
  (f) a light detector for measuring luminescence emitted by said system to determine the presence or quantity of the analyte of interest in the sample.

43. The system of claim 42, wherein said particles are selected from the group consisting of polymeric particles, inorganic particles, metallic particles, metal oxide particles, composite particles and mixtures thereof.

44. The system of claim 42, wherein said particles have a diameter of 0.5 μm to 10 μm.

45. The system of claim 42, wherein said analyte of interest and said particles are different.

46. The system of claim 42, wherein said light detector is adapted to measure luminescence emitted by said label compound in the presence of said particles.

47. The system of claim 42, wherein said voltage source is adapted to induce said electrochemiluminescence in the presence of said particles.

48. A heterogeneous assay method based upon a specific binding reaction and an electrochemiluminescent phenomenon comprising the steps of:
  (a) forming an assay mixture containing:
    (i) a sample containing a first quantity of an analyte of interest having binding properties;
    (ii) a reagent comprising a plurality of inanimate particles which (A) have a surface capable of specifically binding to said analyte of interest or (B) are attached to a second quantity of the analyte of interest or an analog of the analyte of interest; and
    (iii) a label reagent substance selected from the group consisting of (A) the second quantity of the analyte of interest or an analog of the analyte of interest, and (B) a binding partner of the analyte of interest or its said analog, said label reagent substance including a chemical moiety having electrochemiluminescent properties;
  (b) incubating said assay mixture to permit binding;
  (c) separating said particles from said assay mixture;
  (d) causing the label reagent substance to electrochemiluminesce in a electrochemiluminescence cell; and
  (e) measuring luminescence emitted by said label reagent substance and correlating said measurement to a standard to determine whether or not, or in what amount, the analyte of interest is present in the sample.

49. An assay composition for an assay based upon a binding reaction and an electrochemiluminescent phenomenon comprising:
  (a) an electrolyte,
  (b) a sample containing an analyte of interest having binding properties,
  (c) a reagent comprising a plurality of particles having a surface which is: (i) capable of binding to a component of said assay composition or (ii) is linked to said analyte of interest or its analog, wherein said particles and said analyte are different,
  (d) a label substance having binding properties, said label substance including a chemical moiety having electrochemiluminescent properties, and
  (e) a reductant that under oxidizing conditions interacts with the label compound to generate electrochemiluminesce, wherein said assay composition is suitable for use in said assay based on said electrochemiluminescent phenomenon.

50. The composition of claim 49, wherein said composition is in an electrochemiluminescent cell.

51. An assay reagent for use in an assay method for detecting an analyte of interest in a sample using an electrochemiluminescent phenomenon, which assay reagent comprises:
   (a) at least one assay reagent component selected from the group consisting of:
      (i) analyte of interest or an analog of the analyte of interest,
      (ii) a binding partner of the analyte of interest or its said analog, and
      (iii) a reactive component capable of binding with (i) or (ii), wherein one of said assay reagent components is linked to a label compound having a chemical moiety capable of being induced to electrochemiluminesce,
   (b) a reagent comprising a plurality of suspended inanimate particles which are: (i) capable of specifically binding with the analyte or (ii) attached to the analyte or its analog, and
   (c) a reductant that under oxidizing conditions interacts with the label compound to generate electrochemiluminescence,
provided that the components of said assay reagent are not reactive with one another during storage so as to impair their function in the intended assay and said assay reagent is suitable for use in said assay method using said electrochemiluminescent phenomenon.

52. An assay reagent as recited in claim 51, further comprising an electrolyte.

53. The reagent of claim 51, wherein said reagent is in an electrochemiluminescent cell.

54. An assay reagent for an assay based upon a binding reaction and an electrochemiluminescent phenomenon comprising:
   (a) an electrolyte,
   (b) a reagent comprising a plurality of particles which: (i) have a surface capable of binding to said analyte or (ii) are attached to said analyte or its analog,
   (c) a label substance selected from the group consisting of (A) added analyte of interest or its analog, (B) a binding partner of the analyte of interest or its said analog, and (C) a reactive component capable of binding with (A) or (B), said label substance including a chemical moiety having electrochemiluminescent properties, and
   (d) a reductant that under oxidizing conditions interacts with the label compound to generate electrochemiluminescence,
wherein said assay reagent is suitable for use in said assay based on said electrochemiluminescent phenomenon.

55. The reagent of claim 54, wherein said reagent is in an electrochemiluminescent cell.

56. A method for the detection or quantitation of an analyte of interest in a sample, which method comprises the steps of:
   (1) forming a composition comprising:
      (a) a sample, which may comprise a first quantity of the analyte of interest;
      (b) at least one reagent substance selected from the group consisting of:
         (i) a second quantity of the analyte of interest or an analog of the analyte of interest, and
         (ii) a binding partner of the analyte of interest or its said analog wherein one of said reagent substances is linked to a label compound capable of being induced to electrochemiluminesce;
      (c) a second reagent comprising a plurality of particles which are: (i) capable of specifically binding with the analyte of interest or (ii) attached to the second quantity of the analyte of interest or its analog, wherein said particles are selected from the group consisting of polymeric particles, inorganic particles, metallic particles, metal oxide particles, composite particles and mixtures thereof;
   (2) introducing said composition into an electrochemiluminescence cell; and
   (3) inducing the label compound to electrochemiluminesce in said composition in the presence of said particles in said electrochemiluminescence cell; and
   (4) measuring luminescence emitted by the label compound in the presence of said particles to determine whether or not, or in what amount, the analyte of interest is present in the sample.

57. A method for the detection and quantitation of an analyte of interest in a sample, which method comprises the steps of:
   (1) forming a composition comprising:
      (a) a sample,
      (b) a known amount of at least one reagent substance selected from the group consisting of:
         (i) added analyte of interest or an analog of the analyte of interest, and
         (ii) binding partner of the analyte of interest or its said analog, wherein one of said reagent substances is linked to a label compound capable of being induced to electrochemiluminesce, and
      (c) a known amount of a second reagent comprising particles which are: (i) capable of specifically binding with the analyte or (ii) attached to the analyte or its analog, wherein said particles and said analyte are different;
   (2) introducing said composition into an electrochemiluminescence cell;
   (3) inducing the label compound to electrochemiluminesce in said composition in the presence of said particles in said electrochemiluminescence cell; and
   (4) comparing the luminescence emitted by the label compound to the luminescence of a calibration standard to determine whether or not, or in what amount, the analyte of interest is present in the sample.

58. An assay reagent for an assay based upon a binding reaction and an electrochemiluminescent phenomenon comprising:
   (a) at least one reagent substance selected from the group consisting of:
      (i) added analyte of interest or an analog of the analyte of interest,
      (ii) a binding partner of the analyte of interest or its said analog, and
      (iii) a reactive component capable of binding with (i) or (ii) wherein one of said reagent substances is linked to a label compound capable of being induced to electrochemiluminesce,
   (c) a second reagent comprising a plurality of particles which (i) have a surface capable of binding with the analyte or (ii) are attached to the analyte or its analog, and
   (d) a reductant that under oxidizing conditions interacts with the label compound to generate electrochemiluminesce, wherein said assay reagent is suitable for use in said assay based on said electrochemiluminescent phenomenon.

59. The reagent of claim 58, wherein said reagent is in an electrochemiluminescent cell.

60. An assay composition for use in an assay based upon a binding reaction and an electrochemiluminescent phenomenon comprising:
   (a) a sample;
   (b) at least one reagent substance selected from the group consisting of:
      (i) added analyte of interest or an analog of the analyte of interest,
      (ii) a binding partner of the analyte of interest or its said analog, and
      (iii) a reactive component capable of binding with (i) or (ii), wherein one of said reagent substances is linked to a label compound capable of being induced to electrochemiluminesce,
   (c) a second reagent comprising a plurality of particles which (i) have a surface capable of binding with the analyte or (ii) are attached to the analyte or its analog, and
   (d) a reductant that under oxidizing conditions interacts with the label compound to generate electrochemiluminescence,
wherein said assay composition is suitable for use in said assay based on said electrochemiluminescent phenomenon.

61. The composition of claim 60, wherein said composition is in an electrochemiluminescent cell.

62. An assay kit containing reagents for use in a particle-based electrochemiluminescence binding assay for determining the presence or amount of an analyte of interest, comprising, in one or more vessels, the following:
   (a) at least one reagent substance selected from the group consisting of
      (i) added analyte of interest or an analog of the analyte of interest,
      (ii) a binding partner of the analyte of interest or its said analog, and
      (iii) a reactive component capable of binding with (i) or (ii), wherein one of said reagent substances is linked to a label compound capable of being induced to electrochemiluminesce,
   (b) a second reagent comprising a plurality of particles which: (i) have a surface capable of binding with the analyte or (ii) are attached to the analyte or its analog, and
   (c) a reductant that under oxidizing conditions interacts with the label compound to generate electrochemiluminescence,
wherein said assay kit is suitable for use in said assay based on said electrochemiluminescent phenomenon.

63. The assay kit of claim 62, wherein said particles are selected from the group consisting of polymeric particles, inorganic particles, metallic particles, metal oxide particles, composite particles and mixtures thereof.

64. The assay kit of claim 62, wherein said particles have a diameter of 0.5 $\mu$m to 10 $\mu$m.

65. The assay kit of claim 62, wherein said analyte of interest and said particles are different.

66. A method for the detection and quantitation of an analyte of interest in a sample, which method comprises the steps of:
   (a) forming a composition comprising:
      (i) a sample,
      (ii) a first reagent comprising a binding partner of the analyte of interest, wherein said binding partner is linked to a label compound capable of being induced to electrochemiluminesce, and
      (iii) a second reagent capable of specifically binding with the analyte, said second reagent comprising particles selected from the group consisting of polymeric particles, inorganic particles, metallic particles, metal oxide particles, composite particles and mixtures thereof;
   (b) inducing the label compound to electrochemiluminesce; and
   (c) measuring luminescence emitted by the label compound to determine whether or not or in what amount, the analyte of interest is present in the sample.

67. The method of claim 66, wherein said composition is introduced into an electrochemiluminescence cell prior to step (b) and said label compound is induced to electrochemiluminesce in said electrochemiluminescence cell.

68. The method of claim 66, wherein said composition is introduced into an electrochemiluminescence cell prior to step (b) and said label compound is induced to electrochemiluminesce in the presence of said particles in said electrochemiluminescence cell.

69. The method of claim 66, wherein said luminescence is measured from said label compound in the presence of said particles.

70. The method of claim 66, wherein said luminescence is measured from said label compound in said composition in the presence of said particles.

71. The method of claim 66, further comprising separating said particles from said composition, wherein said luminescence is measured from said label compound in said composition in the absence of said particles.

72. The method of claim 66, wherein said particles have a diameter of 0.05 $\mu$m to 200 $\mu$m.

73. The method of claim 66, wherein said particles have a diameter of 0.1 $\mu$m to 100 $\mu$m.

74. The method of claim 66, wherein said particles have a diameter of 0.5 $\mu$m to 10 $\mu$m.

75. The method of claim 66, wherein said analyte of interest is selected from the group consisting of pharmaceutical, hormone, virus, prion, viroid, antibody, antigen, hapten, fatty acid, nucleic acid, protein, lipoprotein, polysaccharide, lipopolysaccharide, glycoprotein, peptide, polypeptide, cellular metabolite, nonbiological polymer, synthetic organic molecule, organometallic molecule, tranquilizer, barbiturate, alkaloid, steroid, vitamin, amino acid, sugar, lectin, recombinant or derived protein, biotin, avidin, streptavidin, and inorganic molecule.

76. The method of claim 66, wherein said method for the detection and quantitation of an analyte is a hybridoma screening assay wherein said analyte of interest is a monoclonal antibody directed against a particular antigen.

77. A method for the detection and quantitation of an analyte of interest in a sample, which method comprises the steps of:
   (a) forming a composition comprising:
      (i) a sample,
      (ii) a first reagent comprising a binding partner of the analyte of interest, wherein said binding partner is linked to a label compound capable of being induced to electrochemiluminesce, and
      (iii) a second reagent linked to added analyte of interest or its analog, said second reagent comprising particles selected from the group consisting of polymeric particles, inorganic particles, metallic particles, metal oxide particles, composite particles and mixtures thereof;

(b) inducing the label compound to electrochemiluminesce; and
(c) measuring luminescence emitted by the label compound to determine whether or not, or in what amount, the analyte of interest is present in the sample.

78. A method for the detection and quantitation of an analyte of interest in a sample, which method comprises the steps of:
(a) forming a composition comprising:
  (i) a sample,
  (ii) a first reagent comprising a binding partner of the analyte of interest, wherein said binding partner is linked to a label compound capable of being induced to electrochemiluminesce, and
  (iii) a second reagent linked to added analyte of interest or its analog, said second reagent comprising particles selected from the group consisting of polymeric particles, inorganic particles, metallic particles, metal oxide particles, composite particles and mixtures thereof;
(b) inducing the label compound to electrochemiluminesce; and
(c) measuring luminescence emitted by the label compound in the presence of said particles to determine whether or not or in what amount, the analyte of interest is present in the sample.

79. The method of claim 1, 4, 56 or 57, wherein said composition further comprises a reductant that under oxidizing conditions interacts with the label compound to generate electrochemiluminesce.

80. The method of claim 22 or 25, wherein said electrochemiluminescence is measured in the presence of said particles.

81. The method of claim 22, 24, 25, or 48, wherein said assay mixture further comprises a reductant that under oxidizing conditions interacts with the label compound to generate electrochemiluminesce.

82. The method of claim 1, 2, 22, 24, 25, 48, or 57 wherein said particles are selected from the group consisting of polymeric particles, inorganic particles, metallic particles, metal oxide particles, composite particles and mixtures thereof.

83. The method of claim 1, 4, 22, 24, 25, 48, 56, or 57, wherein said particles are capable of attenuating the luminescence emitted by the label compound when bound to the label compound.

84. The method of claim 1, 4, 22, 24, 25, 48, 56, or 57 wherein said particles have a diameter of 0.5 $\mu$m to 10 $\mu$m.

85. The assay composition of claim 26, 49, or 60, wherein said particles are selected from the group consisting of polymeric particles, inorganic particles, metallic particles, metal oxide particles, composite particles and mixtures thereof.

86. The assay composition of claim 26, 49, or 60, wherein said particles have a diameter of 0.5 $\mu$m to 10 $\mu$m.

87. The assay composition of claim 26 or 60, wherein said analyte of interest and said particles are different.

88. The assay reagent of claim 51, 54 or 58, wherein said particles are selected from the group consisting of polymeric particles, inorganic particles, metallic particles, metal oxide particles, composite particles and mixtures thereof.

89. The assay reagent of claim 51, 54 or 58, wherein said particles have a diameter of 0.5 $\mu$m to 10 $\mu$m.

90. The assay reagent of claim 51, 54 or 58, wherein said analyte of interest and said particles are different.

91. The method of claim 22, 25, 48, 56, 66, 77, or 78, wherein said analyte of interest and said particles are different.

92. The kit of claim 36 or 41, wherein said label compound is a labeled binding partner of the analyte of interest.

93. The kit of claim 36 or 41, wherein said label compound comprises a metal-containing ECL moiety.

94. The kit of claim 36 or 41, wherein said label compound comprises a metal chelate containing ruthenium or osmium.

* * * * *